United States Patent [19]

Suni et al.

[11] Patent Number: 4,777,127

[45] Date of Patent: Oct. 11, 1988

[54] HUMAN RETROVIRUS-RELATED PRODUCTS AND METHODS OF DIAGNOSING AND TREATING CONDITIONS ASSOCIATED WITH SAID RETROVIRUS

[75] Inventors: Jukka Suni; Antti Vaheri, both of Helsinki, Finland

[73] Assignee: Labsystems Oy, Helsinki, Finland

[21] Appl. No.: 781,478

[22] Filed: Sep. 30, 1985

[51] Int. Cl.[4] .................. C12Q 1/70; G01N 33/543; G01N 33/545

[52] U.S. Cl. .................................. 435/5; 436/518; 436/531; 436/813; 436/822; 530/300; 530/327; 530/328; 530/387; 530/820; 530/826; 530/827; 530/828

[58] Field of Search ............ 530/300, 327, 328, 387, 530/820, 826, 827, 828; 435/5; 436/518, 531, 813, 822

[56] References Cited

U.S. PATENT DOCUMENTS 4,629,783  12/1986  Cosand ........................... 530/324

OTHER PUBLICATIONS

Suni, J. et al., Int. Jour. Cancer 28(5): 559–566 (1981).
Sutcliffe, J. G. et al., Nature, 287: 801–805 (1980).
Hudson, L. et al., in "Practical Immunology" (Blackwell Scientific Publications, Oxford) pp. 5–9, (1980).
T. I. Bonner et al., "Cloned Endogenous Retroviral Sequences from Human DNA", 79 Proc. Natl. Acad. Sci. U.S.A., 4709–4713 (Aug. 1982).
S. J. O'Brien et al., "Mapping of Endogenous Retroviral Human Chromosome 18", 303 Nature 74–77 (May 1983).
K. Robbins et al., "In Vivo Identification of Transforming Gene Product of Simian Sarcoma Virus", 218 Science 1131–1133 (Dec. 1982).
T. Wahlstrom et al., "Monoclonal Antibody Defining a Human Syncytiotrophoblastic Polypeptide Immunologically Related to Mammalian Retrovirus Structural Protein p 30", 5 Placenta 465–474 (Oct. 1984).
J. Suni et al., "Human Placental Syncytiotrophoblastic Mr 75,000 Polypeptide Defined by Antibodies to a Synthetic Peptide Based on a Cloned Human Endogenous Retroviral DNA Sequence", 81 Proc. Natl. Acad. Sci. U.S.A. 6197–6201 (Oct. 1984).

*Primary Examiner*—Robert J. Warden
*Assistant Examiner*—Jack Spiegel
*Attorney, Agent, or Firm*—Hopgood, Calimafde, Kalil, Blaustein & Judlowe

[57] ABSTRACT

A human endogenous retrovirus-related Mv-75,000 protein, containing the decapeptide sequence Glutamic Acid-Asparagine-Proline-Serine-Glutamine-Phenylalanine-Tyrosine-Glutamic Acid-Arginine-Leucine, a synthetic undecapeptide Sp-23 based on the decapeptide, and specific polycolonal and monoclonal antibodies and specific nucleic acid probes are used as specific reagents for the detection and treatment of tumors such as renal cell adenocarcinoma and choriocarcinoma, among others, and placental disorders including blighted ova, hydatiform and destructive moles.

13 Claims, No Drawings

HUMAN RETROVIRUS-RELATED PRODUCTS AND METHODS OF DIAGNOSING AND TREATING CONDITIONS ASSOCIATED WITH SAID RETROVIRUS

FIELD OF THE INVENTION

This invention relates to a human retrovirus-related protein, a decapeptide contained within said protein, a synthetic undecapeptide based on said decapeptide, antibodies raised against these polypeptides, and nucleic acid probes based on the amino acid sequence of these polypeptides. These products are useful in the diagnosis and treatment of certain human diseases.

BACKGROUND OF THE INVENTION

Retroviruses contain RNA as their genomic material. RNA may be transcribed to double-standard DNA form via an enzyme known as reverse transcriptase. When the viral DNA is incorporated into the genomic DNA of a host cell, it is called a provirus (also known as an endogenous retrovirus). As a consequence, the viral gene is replicated along with the cell chromosome and is thus expressed not only in the original, but in all of its progeny. A complete provirus consists of three distinct genes (gag, pol, env) as well as regulatory elements known as long terminal repeates (LTR) at both ends of the provirus. The gag gene codes for structural proteins of the virus, the pol gene codes for the reverse transcriptase enzyme and the env gene codes for envelope glycoproteins. All these genes are transcribed when a complete infectious endogenous retrovirus is produced. However, in many instances, only part of proviral DNA is transcribed and translated, i.e., only gag and pol genes, thus producing an incomplete virus.

Endogenous retroviruses are ubiquitous in animals. They have been recovered from several primates. A major source for isolation of endogenous retrovirus from baboons is the placenta. Particles resembling type C or type D retroviruses have also been seen budding from the syncytiotrophoblast layer of human placentas and from cultured teratocarcinoma cells. In addition, small retrovirus-like particles have been seen in human oocytes. Human endogenous retroviruses have not been isolated in an infectious form and producer cell lines have not been established.

Evidence has been presented that human DNA contains retrovirus-related nucleotide sequences. Nucleic acid reassociation studies first revealed that humans and other primates contain multiple baboon endogenous virsu (BaEV) related sequences in their chromosomal DNA. See, for example, Benveniste, R. E. & Todaro, G. J., *Proc. Natl. Acad. Sci. USA*, Vol. 71, pp. 4513-4518 (1974). A defective, endogenous provirus was isolated from a human recombinant DNA library by using an endogenous chimpanzee retroviral pol fragment as probe. The structure of this fragment is highly related to that of BaEV. This genome, termed HC-20 (or endogenous retrovirus-1; erv-1), has been assigned to human chromosome 18. See O'Brien, S. J., Bonner, T. I., et al., *Nature (London)*, Vol. 303, pp. 74-77 (1983). The erv-1 provirus contains gag and pol genes, which are significantly related to those of both Moloney murine leukemia virus (Mo-MuLV) and BaEV, env related sequences of the expected length, and a 3' long terminal repeat (LTR), but no 5' LTR.

It is known that human placental syncytiotrophoblasts contain an antigen which is detected by a specific polyclonal antibody against the major structural protein p30 of the feline endogenous retrovirus RD114 which is highly related to BaEV. See, Suni, J., Wahlstrom, T., & Vaheri, A., *Int. J. Cancer*, Vol. 28, pp. 559-566 (1981). A study of 1540 human cord blood sera revealed the presence of RD114 p30 reactive antibodies in 118 (7.7%) sera. Antibodies to synthetic peptides, which were based on MuLV p30 amino acid sequences or sequences of env genes, have been found to be reactive with the native structural proteins of murine retroviruses.

The presence of these antibodies in the cord blood sera is highly correlated ($p<0.00005$) to complications during pregnancy and to the number of previous abortions. The antigen, reactive with the antibodies to RD114 p30, is also detected in the tumor cells of renal calls adenocarcinoma, also known as hypernephroma. In immunohistochemical staining this antigenic material can be seen also in the lumen of proximal tubuli of the kidneys as a sign of its excretion to urine. Using a radioimmunoassay, with RD114 virus p30 protein and its specific antibody as reagents, antigenic material can be shown to be excreted into the urine of renal cell adenocarcinoma patients but not of normal individuals.

In 1975, Kohler and Milstein develoed a method of establishing a continuous hybrid cell line (hybridoma) derived by the fusion of murine myeloma cells to spleen cells from an immunized mouse which secreted a monoclonal antibody which binds to only one antigenic site; *Nature*, Vol. 256, p. 495 (1975). This method has subsequently been used by those familiar with the art to derive different kinds of monoclonal antibodies, See, for example, Melchers, F., Potter, M., et al., "Lymphocyte Hybridomas", *Current Topics in Microbiology and Immunology*, Vol. 81 (1978). Some compounds may not be immunogenic unless coupled to a carrier which is itself immunogenic; see, for example, Eisen, H. N., *Immunology*, Harper & Row (1980). Such compounds are called haptens and there are many methods known for attaching them to carriers in order to render the hapten immunogenic.

These methods may be used to create monoclonal or polyclonal antibodies to an undecapeptide, which has partial sequence homology to MuLV and BaEV-p30 proteins. The undecapeptide sequence was inferred from the nucleotide sequence of the human proviral locus, erv-1. These antibodies detect a polypeptide antigen in syncytiotrophoblastic cells of human placentas both in vivo and in culture.

SUMMARY OF INVENTION

A decapeptide, deduced from the gag portion of erv-1 has been isolated. From this, an undecapeptide (Sp-23) which contains the decapeptide as residues 2 through 11 has been synthesized.

A polyclonal antibody raised against the undecapeptide in rabbits has detected a human retrovirus-related $M_r$ 75,000 protein. This protein contains the above decapeptide.

Polyclonal antibodies have been raised against the decapeptide, Sp-23 and the $M_r$ 75,000 protein. These antibodies are used as specific reagents for the detection of tumors such as renal cell adenocarcinoma and choriocarcinoma, among others, and placental disorders including blighted ova, hydatidiform and destructive moles.

DETAILED DESCRIPTION OF THE INVENTION

Based on the gag portion of the human DNA sequence erv-1, a decapeptide has been deduced which has the sequence Glu-Asn-Pro-Ser-Gln-Phe-Tyr-Glu-Arg-Leu.

An undecapeptide (NH$_2$-Cys-Glu-Asn-Pro-Ser-Gln-Phe-Tyr-Glu-Arg-Leu-COOH) was synthesized by using the solid-phase method; Barany, G. & Merrifield, R. B. (1980) in *The Peptides*, eds., Gross, E. & Meienhofer, J. (*Academic, New York*), Vol. 2, pp. 1–282. Residues 2-11 of the peptide sequence were deduced from the nucleotide gag sequence of the human proviral locus, erv-1; Bonner, T. I., O'Connell, C. & Cohen, M. (1982), *Proc. Nat. Acad. Sci. USA* 79, 4709–4713. The sequence of this synthetic peptide (Sp23) fits 6 of 10 with the BaEV p30 and 7 of 10 with the Mo-MuLV p30 sequence (Table 1).

TABLE 1

| Peptide | Sequence homology of Sp23 undecapeptide with defined Retrovirus p24–p30 proteins |
|---|---|
| Sp23 (HC-20, human DNA) | Cys—<u>Glu</u>—<u>Asn</u>—<u>Pro</u>—<u>Ser</u>—<u>Gln</u>—<u>Phe</u>—<u>Tyr</u>—<u>Glu</u>—<u>Arg</u>—<u>Leu</u> |
| MuLV (murine) | —<u>Glu</u>—Ser—<u>Pro</u>—<u>Ser</u>—Ala—<u>Phe</u>—Leu—<u>Glu</u>—<u>Arg</u>—<u>Leu</u> |
| BaEv (baboon) | —<u>Glu</u>—Ser—<u>Pro</u>—Ala—Ala—<u>Phe</u>—Met—<u>Glu</u>—<u>Arg</u>—<u>Leu</u> |
| SSAV (woolly monkey) | —<u>Glu</u>—Pro—<u>Pro</u>—<u>Ser</u>—Val—<u>Phe</u>—Leu—<u>Glu</u>—<u>Arg</u>—<u>Leu</u> |
| HTLV (human) | —<u>Glu</u>—Pro—Tyr—His—Ala—<u>Phe</u>—Val—<u>Glu</u>—<u>Arg</u>—<u>Leu</u> |

Homologies with Sp23 are underlined. In the original publication Bonner, T.I., O'Connell, C. & Cohen, M. (1982), Proc. Natl. Acad. Sci. USA 79, 4709–4313, leucine and tyrosine residues in the seventh positions were inadvertently switched between the human and MuLV sequence. SSAV, simian sarcoma-associated virus; HTLV, human T-cell leukemia virus.

An unrelated synthetic undecapeptide (Sp49) was prepared by using the same method. In additiona, an unrelated synthetic dodecapeptide (LSp2) (Universal Biochemicals, Cambridge, U.K.) was used.

Since the undecapeptide is a hapten, it is necessary to first conjugate the hapten to a high molecular weight carrier to obtain an immunogen. Such carriers include proteins, polysaccharides, and various latex particles. For the purpose of the present invention the undecapeptides were conjugated to keyhole limpet hemocyanin by using m-maleimidobenzoyl-N-hydroxysuccinimide ester as the coupling reagent; Liu, F. T., Zinnecker, M., Hamaoka, T. & Katz, D. H. (1979), *Biochemistry* 18, 690–697; and were used to immunize rabbits from which preimmune sera had been collected by using three subcutaneous injections of 100 micrograms of the peptide in Freund's incomplete adjuvant at 2-week intervals. The rabbits were bled 10 days later.

The antibody obtained detects by immunohistochemical staining using peroxidase-antiperoxidase antibody conjugates an antigen in syncytiotrophoblastic cells of first trimester placentas, blighted ova, hydatidiform and destructive moles, choriocarcinoma, and renal cell adenocarcinoma but not normal kidney tissue.

To culture and isolate trophoblastic cells, human choriocarcinoma JAr; Pattillo, R. A., Ruckert, A., Hussa, R., Bernstein, R. & Delfs, E. (1971), *In Vitro* 6, pp. 398-399, BeWo (ATCC CCL98, Amercian Type Culture Collection), and JEG-3 cells (ATCC HTB 36), all known to secrete human chorionic gonadotropin, were grown as monolayer cultures in Eagle's minimal essential medium (ME medium) supplemented with 10% fetal bovine serum. Under these conditions, 1-2% of the cells had a syncytiotrophoblastic morphology; the rest of the cells were cytotrophoblast-like. Adult human skin fibroblasts of a strain established in our laboratory, Vaheri, A., Kurkinen, M., Lehto, V. P., Linder, E. & Timpl, R. (1978), *Proc. Natl. Acad. Sci. USA* 75, 4944–4948, were grown in the same medium.

Syncytiotrophoblastic cells were isolated from the first-trimester placentas received from elective abortions (based on socioeconomic grounds). The trophoblast isolation procedure described in detail by Saksela, O., Wahlstrom, T., Lehtovirta, P., Seppala, M. & Vaheri, A. (1981), *Cancer Res.* 41, 2501–2513, is briefly described as follows. The placenta was washed with Dulbecco's phosphate-buffered saline supplemented with antibiotics followed by sectioning with scissors and treatment with a mixture of collagenase/-hyaluronidase/soybean trypsin inhibitor. The separation of the loosened trophoblastic cells from placental matrix was performed by successive filtration through iron mesh (1×1 mm) and cotton mesh (30 μm) in which the large syncytiotrophoblastic cells were entrapped. The cells were rinsed from the mesh with ME medium supplemented with 10% fetal bovine serum and penicillin/streptomycin. The isolated cells were sedimented with low-speed centrifugation and the pellet was frozen at −20° C. until use.

Immunoperoxidase staining of 38 normal placentas, the gestation time of which varied from 5 to 41 weeks, 10 blighted ova, 10 hydatidiform moles, 10 destructive moles, and 10 choriocarcinomas was performed on 4-μm-thick tissue sections in which endogenous peroxidase activity had been destroyed by incubation at room temperture for 30 minutes in methanol containing 0.3% hydrogen peroxide. The antisera were diluted 1:100 in phosphate-buffered saline, and the avidin-biotinperoxidase method (Vectastain ABC Kit, Vector Laboratories, Burlingame, Calif.), as recommended by the manufacturer, was employing using 3-amino-9-carbazole as the chromogenic enzyme substrate. The cover glasses were mounted with Aquamount (Gurr, Hopkin & Williams, Chadwell Heath, England).

A large variety of other normal tissues, of both adult and fetal origin, including skin, brain, parotic gland, lung, heart, spleen, liver, muscle, adrenal gland, ovary, Fallopian tube, uterus, urinary bladder, prostate, and testis, were also studied.

For immunoblotting, the isolated syncytiotrophoblastic cells from placentas and cultured cells or purified retroviruses [BaEv, MuLV, SSAV, and avian myeloblastosis virus (AMV); the latter purchased from Life Sciences, St. Petersburg, FL] were treated as follows. The cells were directly dissolved in Laemmli sample buffer. The proteins were separated by NaDodSO$_4$/-polyacrylamide gradient (5–16%) slab gel electrophoresis (NaDodSO$_4$/PAGE) according to Laemmli, Laemmli, U.K. (1970) *Nature* (*London*) 227, 680–685, with reducing conditions. After separation the proteins were transferred electrophoretically to a nitrocellulose sheet and immunoblotted according to the procedure by Towbin et al., Towbin, H., Staehelin, T. & Gordon, J. (1979), *Proc. Natl. Acad. Sci. USA* 76, 4350–4354, modified as described, Vartio, T., Zardi, L., Balza, E. Towbin, H. & Vaheri, A. (1982) *J. Immunol. Methods* 55, 309–318. For the immunological staining of the transferred proteins, the specific and control antibodies were diluted 1:500 in TEn-Tx buffer (50 mM Tris HCl. pH 7.0/5 mM NaCl/0.05% Triton X-100). The immunoreactive polypeptide bands were visualized by using the Vectastain ABC kit as described above. In some experiments immunological detection of bound antibodies was with $^{125}$I-labeled protein A followed by autoradiography, Towbin, H. Staehelin, T. & Gordon, J. (1979) *Proc. Natl. Acad. Sci. USA* 76, 4350–4354.

In control experiments, anti-Sp23 diluted 1:100 was mixed with disrupted (0.01% Triton X-100 and ultrasonic treatment) purified BaEV or AMV, 100 μg of protein per ml. incubated for 1 hour at room temperature in an end-over mixer, then incubated at +4° C. overnight, and then used for immunoblotting at a final 1:500 dilution of anti-Sp23. In a second series of similar control experiments, anti-Sp23 diluted 1:500 was mixed with 2 or 0.2 μg of Sp23 or of an unrelated dodecapeptide (LSp2) per ml incubated as above and used for immunoblotting.

EXAMPLE I

Results of Immunoblotting of Cultured Choriocarcinoma Cells

Immunoblotting of JEG-3 choriocarcinoma cells with anti-Sp23 detected a major polypeptide at $M_r$ 75,000 from proteins separated by NaDodSO$_4$/PAGE under reducing or nonreducing conditions and transferred onto a nitrocellulose sheet. In addition, a doublet of polypeptides at $M_r$ 100,000–110,000 reacted with anti-Sp23. The relative intensity of the doublet to that of the $M_r$ 75,000 polypeptide varied but was always lower. Similar results were obtained with proteins of JAr and BeWo chroiocarcinoma cells but not with human fibroblasts or several other control cells. Under the same experimental conditions anti-Sp23 detected from proteins of isolated placental syncytiotrophoblastic cells have a similar $M_r$ 75,000 polypeptide. The doublet seen in immunoblots of choriocarcinoma cells was not obtained from the proteins of syncytiotrophoblasts. These findings were obtained regularly by using choriocarcinoma cells grown to different passage levels and by using syncytiotrophoblasts isolated from individual human first-trimester placentas. Sera from two anti-Sp23 rabbits gave similar results. A preimmunue serum and a control antiserum raised against an unrelated undecapeptide gave constantly negative results. Anti-Sp23 pretreated with the synthetic peptide Sp23 did not react with the $M_r$ 75,000 polypeptide; pretreatment with an unrelated synthetic dodecapeptide, with disrupted BaEv or with disrupted AMV, had no effect on the reactivity of anti-Sp23. The reactivity of this antibody with the $M_r$ 75,000 protein in this immunoblotting assay can be partially blocked by pretreatment of the antibody with the synthetic peptide Sp23 at a concentration of 0.2 ug/ml and totally blocked when the peptide is used at a concentration of 2.0 ug/ml.

EXAMPLE II

Results of Reactivity of Auto-Sp-23 With Normal and Malignant Human Placenta Tissue Immunoperoxidase staining of tissue sections with anti-Sp23 gave a strong reaction for the syncytiotrophoblastic cells of all early (<15 wk) placentas examined but not for older placentas and for all other normal tissues studied (Table 2). The typical pattern of staining was scattered and localized predominantly to large multinuclear syncytiotrophoblasts. In addition, occasional cells with cytotrophoblastic morphology were positive. The staining was, in both types of cells, diffuse and confined to the cytoplasm with no apparent enrichment to the cell surface. When in the staining procedure, anti-Sp23 was replaced with the preimmune rabbit serum, the antibody to an unrelated synthetic undecapeptide, or a buffer control, consistently negative results were obtained.

In benign (hydatidiform mole) and malignant placental tumors (destructive mole, choriocarcinoma) cells with trophoblastic morphology reacted with anti-Sp23 (Table 2) but not with the controls.

TABLE 2

| Immunoperoxidase staining of tissue sections with the anti-Sp23 serum | | |
|---|---|---|
| Tissue | No. of Specimens Tested | No. Positive |
| Human placental syncytiotrophoblast | | |
| 5–15 wk | 17 | 17 |
| 16–41 wk | 21 | 0 |
| Blighted ova | 10 | 10 |
| Hydatidiform mole | 10 | 10 |
| Destructive mole | 10 | 10 |
| Choriocarcinoma | 10 | 10 |
| Normal embryonal (16–24 wk) | * | 0 |
| Normal adult | * | 0 |

The $M_r$ 75,000 protein has been purified to homogeneity from cultured choriolcarcinoma cells using treatment with the non-ionic detergent Triton X-114 (p-iso-Octylpolyoxy ethylene phenol polymer), and gel permeation and ion-exchange columns in high performance liquid chromatography. In a preferred embodiment, human choriocarcinoma JEG-3 cells (ATCC HTB36) known to secrete human chorionic gonadotropin were grown in roller bottles as monolayer culture in Eagle's minimal essential medium (ME medium) supplemented with 10% fetal bovine serum. Cells were harvested in Ten-TX 114 buffer (50 mM Tris-HCl pH 7.4, 10 mM EDTA 150 mM NaCl and 1% Tx 114). Insoluble material was separated by centrifugation 10000 g for 20'. Collected supernatant was filtered through 0.22 um filter.

The filtrate was fractionated with TSK 3000 gel permeation column (Toyo Soda) using Variant HPLC system. Running buffer was 50 mM Tris-HCl pH 6.5 and 150 mM NaCl 3.5 ml/min. 3 ml fractions were collected and were tested with immunoblotting using anti-Sp23 antibody. Positive fractions were lyophilized and dissolved in small volume of distilled water. Buffer was exchanged to 20 mM Tris-HCl pH 7.5 using Pharmacia PD 10 column.

The anion exchange was carried out with Pharmacia Mono Q column and Pharmacia PD 10 column. Running buffer of 20 mM Tris-HCl pH 7.5 and proteins were eluted with 20 mM Tris-HCl pH 7.9 560 mM NaCl. Fractions were tested with immunoblotting.

After the purification steps the purity of the 75 kD protein was about 95%.

The isolated protein has the mobility of a 75,000-dalton protein in SDS-PAGE and in immunoblotting it reacts specifically with the antibody against the synthetic peptide Sp23.

A polyclonal antibody has been raised against the purified choriocarcinoma cell $M_r$ 75,000 via conventional techniques, for example by immunizing rabbits with the purified protein, bleeding them and extracting the antibody. This antibody detects in immunohistochemical staining an antigen in the same tissues as the antibody against the original synthetic peptide Sp23. In immunoblotting this antibody detects the $M_r$ 75,000 protein.

As stated above, human placental syncytiotrophoblasts contain an antigen which is detected by a specific polyclonal antibody against the major structural protein p30 of the feline endogenous retrovirus RD114, which is highly related to BaEV.

Accordingly, the purified $M_r$ 75,000 protein, as well as the decapeptide deduced from the gag portion of erv-1 and the synthetic peptide Sp-23, may be used as antigens to detect the presence of human antibodies directed against the whole $M_r$ 75,000 protein or art of it. They are therefore effective diagnostic agents. In the antibody detection, the antigen is let to react with a solid phase, e.g., plastic or cellulose derivatives. The reaction of human antibodies with the solid-phase bound antigen may be detected by using radioactive, enzyme, fluorescent or chemiluminescent conjugates. The antibodies may be detected in the serum and other body fluids of patients with gestational disorders, with choriocarcinoma or with renal cell adenocarcinoma.

The specific antigens are used in radioimmunoassay in which the antigen is labelled with radioactive iodine. The labelled antigen is let to compete with the antigen present in patient sample in the presence of specific antibody. The presence of the antigen in the sample is seen as a decrease in the radioactivity bound to the specific antiserum. The antigen may be detected from tissue sample, urine, serum or other body fluids of patients. The antigen detection may be used in monitoring the extent of tumor excision and in the follow-up of recidives and metastases in choriocarcinoma and renal cell adenocarcinoma patients. The antigen may be detected in the serum and amniotic fluid of women with gestational problems.

Polyclonal antibodies have been produced against the isolated intact $M_r$ 75,000 protein as described above.

Polyclonal antibodies have been raised against the synthetic peptide Sp-23 as described above. Polyclonal antibodies may also be raised against the decapeptide as well, using the same technique.

Monoclonal antibodies may also be raised against the Sp-23 peptide, the decapeptide and the $M_r$ 75,000 protein, using the Kohler-Milstein technique. In a preferred embodiment, since the Sp-23 peptide and decapeptide are both haptenes, they are first conjugated to a high molecular weight carrier to obtain an immunogen. Any high molecular weight carrier known in the art is acceptable, including those carriers used in the production of the polyclonal antibody against the Sp-23 peptide.

All these antibodies are used in the detection of the $M_r$ 75,000 protein-specific antigens. These antibodies may be used as primary antisera in immunological staining of histopathological and cell culture specimens. The antibodies are also used in solid-phase immunoassays in the detection and quantification of the $M_r$ 75,000 protein. In these tests one of the antibodies was let to react with a solid phase as described and the reaction of the antigen in patient sample was detected by a second $M_r$ 75,000-specific antibody labelled either with a radioactive, enzyme, fluorescent or chemiluminescent marker. These tests can be used as described.

The $M_r$ 75,000 protein specific monoclonal antibodies may be used in the in vivo diagnosis of choriocarcinoma and renal cell adenocarcinoma patients, especially in the search for distant metastases. The monoclonal antibodies are radioactively labelled and injected into the circulation of a patient. The labelled monoclonal antibody will accumulate to the tumor or its metastases reacting with its $M_r$ 75,000-specific antigen. The reactivity may be detected by a gamma camera.

The monoclonal antibodies against the $M_r$ 75,000 protein may be used as therapeutic agents. The antibodies injected into the circulation of a patient may act as a cytotoxic antibody causing destruction of the tumor by cell-mediated cytotoxicity reaction. These antibodies may be coupled to cytotoxic chemicals; thus these antibodies may be used to accumulate high doses of cytotoxic drugs at the tumors causing specific death of tumor cells.

Based on the amino acid sequence of the $M_r$ 75,000 protein, oligonucleotide probes specific for the gene that encodes the protein can be produced. These probes can be used in nucleic acid hydridization methods, known to those skilled in the art, for example Southern, Northern and in situ hybridizations (Maniatis, et al., Molecular Cloning—A Laboratory Manual, Cold Spring Harbor Laboratory (1982)), to isolate the gene encoding the $M_r$ 75,000 protein from a human DNA library. The isolated gene or fragments can be introduced by recombinant DNA methods into a suitable host, e.g., *E. Coli*, using expression vectors to produce large quantities of the protein or polypeptide fragments thereof. The protein or fragments can be used as antigens in tests or for monoclonal antibody production.

The principles, preferred embodiments and modes of operation of the invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

What is claimed is:

1. A decapeptide, deduced from the nucleotide gag sequence of a human proviral locus endogenous retrovirus-1, which has the peptide sequence of glutamic acid-asparagine-proline-serum-glutamine-phenylalanine-tyrosine-glutamic acid-arginine-leucine.

2. A synthetic undecapeptide denoted Sp-23, whose residues 2 through 11 are deduced from the nucleotide gag sequence of a human proviral locus endogenous retrovirus-1 and which residues have the peptide sequence cysteine-glutamic acid-asparagine-prolineserine-glutamine-phenylalanine-tyrosine glutamic acid-arginine-leucine.

3. A human retrovirus related protein with a molecular weight of about 75,000 daltons and which contains the decapeptide sequence glutamic acid-asparagine-proline-serine-glutamine-phenylalanine-tyrosine-glutamic acid-arginine-leucine, said human retrovirus related protein being in substantially pure form.

4. A human retrovirus related protein with a molecular weight of about 75,000 daltons and which contains the decapeptide sequence glutamic acid-asparagine-proline-serine-glutamine-phenylalanine-tyrosine-glutamic acid-arginine-leucine,
   said human retrovirus related protein being isolated from a tissue sample or body fluid of a human with a gestational disorder, choriocarcinoma or renal cell adenocarcinoma.

5. An antibody produced by immunization with a synthetic undecapeptide denoted Sp-23, whose residues 2 through 11 are deduced from nucleotide gag sequence of the human proviral locus endogenous retrovirus-1 and which has the peptide sequence cysteine-glutamic acid-asparagine-proline-serine-glutamine-phenylalanine-tyrosine-glutamic acid-arginine-leucine, which antibody reacts with the synthetic undecapeptide Sp-23 and a human retrovirus related protein with a molecular weight of about 75,000 daltons which contains a decapeptide sequence glutamic acid-asparagine-proline-serine-glutamine-phenylalanine-tyrosine-glutamic acid-asparagine-proline-serine-glutamine-phenylalanine-tyrosine-glutamic acid-arginine-leucine.

6. An antibody produced by immunization with a decapeptide deduced from the nucleotide gag sequence of a human proviral locus endogenous retrovirus-1 which has the peptide sequence glutamic acid-asparagine-proline serine-glutamine-phenylalanine-tyrosine-glutamic acid-arginine-leucine, which antibody reacts with said decapeptide and a human retrovirus related protein with a molecular weight of about 75,000 daltons which contains the decapeptide sequence glutamic acid-asparagine-proline-serine-glutamine-phenylalanine-tyrosine-glutamic acid-arginine-leucine.

7. An antibody produced by a immunization with a human retrovirus related protein with a molecular weight of about 75,000 daltons which contains the decapeptide sequence glutamic acid-asparagine-proline-serine-glutamine-phenylalanine-tyrosine-glutamic acid-arginine-leucine which antibody reacts with said human retrovirus-related protein.

8. A method of detecting antibodies in human tissue and body fluids against at least a portion of a human retrovirus related protein with a molecular weight of about 75,000 daltons which contains the peptide sequence glutamic acid-asparagine-proline-serine-glutamine-phenylalanine-tyrosine-glutamic acid-arginine-leucine which comprises:
(a) binding an antigen selected from the group consisting of
   i. the human retrovirus-related protein;
   ii. a decapeptide deduced from the nucleotide gag sequence of a human proviral locus endogenous retrovirus-1 which has the peptide sequence glutamic acid-asparagine-proline-serine-glutamine-phenylalanine-tyrosine-glutamic acid-arginine-leucine; and
   iii. a synthetic undecapeptide denoted Sp-23 whose residues 2 through 11 are deduced from the nucleotide gag sequence of a human proviral locus endogenous retrovirus-1 which has the peptide sequence glutamic acid-asparagine-proline-serine-glutamine-phenylalanine-tyrosine-glutamic acid-arginine-leucine;
to a solid phase;
(b) contacting said solid phase bound antigen with a human tissue sample or body fluid; and
(c) detecting a reaction between the human tissue or body fluid and the solid phase bound antigen.

9. The method of claim 8 wherein said human tissue sample or body fluid is selected from the group consisting of kidney, uterus, placenta, serum, urine, and amnionic fluid.

10. The method of claim 8 wherein said antibodies are detected in the tissue sample or body fluid of humans with a condition selected from the group consisting of gestational disorders, choriocarcinoma and renal cell adenocarcinoma.

11. A method of detecting the presence of a human retrovirus related protein with a molecular weight of about 75,000 daltons which contains the peptide sequence glutamic acid-asparagine-proline-serine-glutamine-phenylalanine-tyrosine-glutamic acid-arginine-leucine which comprises:
(a) contacting a histopathological or cell culture specimen with an antibody selected from the group consisting of:
   i. a monoclonal antibody which reacts with the human retrovirus related protein;
   ii. a polyclonal antibody which reacts with the human retrovirus related protein;
   iii. a monoclonal antibody which reacts with a decapeptide deduced from the nucleotide gag sequence of a human proviral locus endogenous retrovirus-1, which has the peptide sequence of glutamic acid-asparagine-proline-serine-glutamine-phenylalanine-tyrosine-glutamic acid-arginine-leucine;
   iv. a polyclonal antibody which reacts with a decapeptide deduced from the nucleotide gag sequence of a human proviral locus endogenous retrovirus-1, which has the peptide sequence of glutamic acid-asparagine-proline-serine-glutamine-phenylalanine-tyrosine-glutamic acid-arginine-leucine;
   v. a monoclonal antibody which reacts with a synthetic undecapeptide denoted Sp-23, whose residues 2 through 11 are deduced from the nucleotide gag sequence of a human proviral locus endogenous retrovirus-1 and which has the peptide sequence cysteine-glutamic acid-asparagine-proline-serine-glutamine-phenylalanine-tyrosine-glutamic acid-arginine-leucine; and
   vi. a polyclonal antibody which reacts with a synthetic undecapeptide denoted Sp-23, whose residues 2 through 11 are deduced from the nucleotide gag sequence of a human proviral locus endogenous retrovirus-1 and which has the peptide sequence cysteine glutamic acid-asparagine-proline-serine-glutamine-phenylalanine-tyrosine-glutamic acid-arginine-leucine;
(b) removing excess antibody, histopathological specimen or cell culture specimen; and
(c) detecting a reaction between the antibody and the histopathological or cell culture specimen.

12. The method of claim 11 wherein said histopathological or cell culture specimen is selected from the group consisting of kidney, uterus or placenta.

13. The methiod of claim 11 wherein said human retrovirus related protein is detected in the histopathological or cell culture specimen of humans with a condition selected from the group consisting of gestational disorders, choriocarcinoma and renal cell adenocarcinoma.

* * * * *